(12) United States Patent
Mathieu et al.

(10) Patent No.: US 6,441,256 B1
(45) Date of Patent: Aug. 27, 2002

(54) METHOD FOR PREPARING OF HALOGENATED HYDROCARBONS

(75) Inventors: Véronique Mathieu, Wavre; Francine Janssens, Vilvoorde, both of (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/485,336
(22) PCT Filed: Jul. 31, 1998
(86) PCT No.: PCT/EP98/04966
§ 371 (c)(1),
(2), (4) Date: Mar. 20, 2000
(87) PCT Pub. No.: WO99/07659
PCT Pub. Date: Feb. 18, 1999

(30) Foreign Application Priority Data

Aug. 8, 1997 (BE) .......................................... 09700669
Jul. 16, 1998 (BE) .......................................... 09800546

(51) Int. Cl.$^7$ ........................ C07C 21/18; C07C 17/26
(52) U.S. Cl. ...................................... 570/172; 570/257
(58) Field of Search ................................ 570/172, 257

(56) References Cited

U.S. PATENT DOCUMENTS

| 3,268,603 A | * | 8/1966 | Goble et al. ................. | 570/257 |
| 3,454,657 A | | 7/1969 | Decker et al. ............... | 260/651 |
| 3,649,698 A | * | 3/1972 | Scherling ................... | 570/257 |
| 3,651,019 A | | 3/1972 | Asscher et al. | |
| 3,862,978 A | | 1/1975 | Decker et al. | |
| 5,446,217 A | | 8/1995 | Van Der Puy et al. | |
| 5,792,893 A | | 8/1998 | Wilson et al. | |
| 5,917,098 A | | 6/1999 | Bertocchio et al. | |

FOREIGN PATENT DOCUMENTS

| EP | 0 729 932 | 4/1996 |
| EP | 0787707 | 8/1997 |
| FR | 1288511 | 5/1961 |
| GB | 1146463 | 3/1969 |
| GB | 2188929 | 10/1987 |
| WO | 95/04021 | 2/1995 |
| WO | 95/04022 | 2/1995 |
| WO | 96/01797 | 1/1996 |
| WO | 97/05089 | 2/1997 |
| WO | 97/07083 | 2/1997 |
| WO | 97/15540 | 5/1997 |
| WO | 98/50329 | 11/1998 |
| WO | 98/50330 | 11/1998 |
| WO | 99/07659 | 2/1999 |

OTHER PUBLICATIONS

Kotora et al., "Addition of Tetrachloromethane to Halogenated Ethenes Catalyzed by Transition Metal Complexes," *Journal of Meolecular Catalysts*, 77:51–60 (1992).

Ullmann's Encyclopedia of Industrial Chemistry, 1992, vol. B4, p. 387–388.

Asscher and Vofsi, *Chlorine Activation by Redox Transfer. Part II. The addition of Carbon Tetrachloride to Olefins*, 1963, pp. 1887–1896.

R. Freidlinda et al., "Telomerization of 2–Chloropropene with Carbon Tetrachloride", Bull. Acad. Sci. USSR, 28, pp. 1766–1769 (1979).

Kotora et al., "Selective Additions of Polyhalogenate Compounds to Chloro Substituted Ethenes Catalyzed by a Copper Complex", React. Kinet. Catal. Lett. 44, No. 2, pp. 415–419 (1991).

T. Asahara et al, Kogyo Kagaku Zasshi, 72:1526–29 (1969).

Belbachir, M. et al, *Makromol. Chem 185*: 1583–1595 (1984).

* cited by examiner

*Primary Examiner*—Alan Siegel
(74) *Attorney, Agent, or Firm*—Connolly Bove Lodge & Hutz LLP

(57) ABSTRACT

Halohydrocarbons comprising at least 3 carbon atoms are obtained by reaction between a haloalkane and a haloolefin, in the substantial absence of nitrile, and by introducing the reactants in a molar ratio between the haloalkane and the haloolefin of less than 2. 1,1,1,3,3-Pentachloropropane can thus be obtained in good voluminal yield.

18 Claims, No Drawings

METHOD FOR PREPARING OF HALOGENATED HYDROCARBONS

This application is an 371 of PCT/EP98/04966 filed Jul. 31, 1998.

The present invention relates to a process for the preparation of halohydrocarbons comprising at least 3 carbon atoms, by catalytic reaction between a haloalkane and a haloolefin.

The addition of a haloalkane to a haloolefin is a well-known reaction. However, it is sometimes difficult to control the reaction such that only one haloolefin molecule adds to a haloalkane molecule (formation of a 1:1 addition product or adduct).

It is generally accepted that a haloalkane/haloolefin molar ratio at least equal to 2 is required in order to obtain high selectivity of 1:1 addition products (see for example T. Asahara et al., Kogyo Kagaku Zasshi, 72 (1969), 1526–9; and M. Belbachir et al., Makromol. Chem., 185 (1984), 1583–95 and patent application PCT 95/04021). However, this excess of haloalkane reduces the voluminal production efficiency of the synthetic process and makes the separation of the reaction products difficult.

Moreover, it is common practice to use a solvent in order suitably to dissolve the catalyst and to increase the reaction yield, although, in doing so, the voluminal production efficiency of the process is also limited. Conventionally, nitrites are used for this purpose, in particular acetonitrile. Thus, patent application PCT 96/01797, which relates to a process for the preparation of fluorohydrocarbons (FHC) starting from chloro precursors, describes the preparation of 1,1,1,3,3-pentachloropropane by telomerization between tetrachloromethane ($CCl_4$) and vinyl chloride (VC), in the presence of acetonitrile. This results in a low voluminal production efficiency (of about 0.1 mol/h.kg),even with a $CCl_4$/VC ratio of 1.7. The presence of a nitrile is also envisaged in the process for the manufacture of a halohydrocarbon by reaction between a haloalkane and a haloalkene, described in patent application PCT 97/07083. In addition, all the examples relate to haloalkane/haloalkene molar ratios of 4 or more. The production efficiencies resulting therefrom are consequently low.

The invention is thus directed towards providing a process for the preparation of halohydrocarbons comprising at least 3 carbon atoms, which no longer has the drawbacks of the known processes, in particular a process in which the 1:1 addition product is obtained with high voluminal selectivity and production efficiency, without diluting the reaction medium, which also makes the subsequent steps for separating the reaction products easier.

Consequently, the present invention relates to a process for the preparation of halohydrocarbons comprising at least 3 carbon atoms, by catalytic reaction, in the substantial absence of nitrile, between a haloalkane and a haloolefin in a haloalkane/haloolefin molar ratio of less than 2.

The process according to the invention can be carried out in a continuous or batchwise manner. It is understood that the molar ratios between the reactants are expressed, in a batchwise process, between the total amounts of reactants used, and, in a continuous process, between the stationary amounts of reactants present in the reactor.

According to the present invention, the molar ratio between the haloalkane and the haloolefin is less than 2. This ratio is generally greater than or equal to 0.7. Advantageously, this ratio is greater than or equal to 0.8. Preferably, it is greater than or equal to 1. Excellent results are obtained when this ratio is at least equal to 1.2. The reason for this is that it has been observed, surprisingly, in the process of the invention, that it is possible to work with a ratio between the haloalkane and the olefin of close to the stoichiometry without appreciably affecting the selectivity.

The process according to the invention is carried out in the substantial absence of organic compounds having a nitrile (C≡N) group. The term substantial absence is understood to mean a weight content, relative to the entire reaction mixture, of less than 2%, preferably of less than 1%, in a particularly preferred manner of less than 0.1%. More particularly, the process according to the invention is carried out in the substantial absence of acetonitrile.

The haloalkanes used in the process according to the present invention are generally saturated organic compounds. They preferably have from 1 to 3 carbon atoms and preferably at least 2 chlorine atoms. They can also comprise other constituents, such as other halogen atoms, alkyl groups or haloalkyl groups. As examples of haloalkanes according to the present invention, mention may be made of dichloromethane, chloroform, carbon tetrachloride, 1,1,1-trichloroethane and 1,1,1-trichloro-2,2,2-trifluoroethane. Carbon tetrachloride is most particularly preferred.

The haloolefins used in the process according to the present invention are generally derivatives of a haloethene or of a halopropene, and preferably correspond to the formula

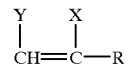

with Y=H or Cl, X=Cl or F and R=H, Cl, F or $CH_3$. Among these compounds, those in which Y=H, X=Cl and R=H or $CH_3$ are preferred.

The halohydrocarbons obtained according to the process of the present invention generally belong to the family of chloropropanes, chlorobutanes or chloropentanes. The carbon atoms in the said chloropropanes, chlorobutanes and chloropentanes can also be substituted with other functional groups, such as other halogen atoms (for instance bromine or iodine atoms), alkyl groups or haloalkyl groups, nitrile (C≡N) groups or carboxylic acid (COOH) groups. Chloropropanes and chlorobutanes which are not substituted with other functional groups are preferred.

Preferably, the halohydrocarbons obtained according to the process of the present invention correspond to the general formula $C_nH_{(2n+2)-p}Cl_p$ in which n is an integer and has the values 3 or 4 and p is an integer which has the values 3 to 7. Examples of compounds obtained according to the process of the present invention are 1,1,1,3,3-pentachloropropane, 1,1,1,3,3-pentachlorobutane, 1,1,1,3-tetrachloropropane, 1,1,3,3-tetrachlorobutane, 1,1,1,3,3,3-hexachloropropane and 1,1-dichloro-2-trichloromethylpropane. Among these compounds, 1,1,1,3,3-pentachloropropane, 1,1,1,3,3-pentachlorobutane, 1,1,1,3,3,3-hexachloropropane and 1,1-dichloro-2-trichloromethylpropane are preferred. 1,1,1,3,3-Pentachlorobutane and 1,1,1,3,3-pentachloropropane are most particularly preferred.

The halohydrocarbons obtained according to the process of the invention are precursors of the corresponding fluoro analogues, which can readily be obtained by treatment with hydrogen fluoride in the presence of a catalyst such as an antimony salt, a titanium salt, a tantalum salt or a tin salt.

The catalytic system used in the present invention preferably comprises at least one copper compound. Advantageously, it is a copper (II) compound. In a particularly preferred manner, this Cu(II) compound is chosen from copper (II) chloride, copper (II) hydroxychloride, copper (II) acetylacetonate and copper (II) hexafluoroacetylacetonate, and mixtures thereof. Excellent results have been obtained with copper (II) hexafluoroacetylacetonate.

The molar ratio between the Cu(II) compound and the olefin is usually greater than or equal to 0.0001. Advantageously, it is greater than or equal to 0.001.

Preferably, it is greater than or equal to 0.005. The molar ratio between the Cu(II) compound and the olefin is usually less than or equal to 1. Advantageously, it is less than or equal to 0.5. Preferably, it is less than or equal to 0.1.

The catalytic system used in the present invention preferably comprises a cocatalyst, in particular an amine, an amide or a trialkylphosphine oxide. As amides which can be used as cocatalyst, mention may be made of N-methylpyrrolidone and N,N-dimethylformamide. As trialkylphosphine oxides which can be used as cocatalyst, mention may be made of the compounds of formula $(R_1R_2R_3)PO$, in which $R_1$, $R_2$ and $R_3$ represent identical or different, preferably linear, C3–C10 alkyl groups. Tri(n-butyl)phosphine oxide, tri(n-hexyl)phosphine oxide, tri(n-octyl)phosphine oxide, n-octyldi(n-hexyl)phosphine oxide and n-hexyldi(n-octyl)phosphine oxide, and mixtures thereof, are selected in particular. It is preferred to use an amine as cocatalyst, in particular a primary amine. Aliphatic amines comprising from 3 to 25 carbon atoms are preferred. Aliphatic amines comprising from 3 to 22 carbon atoms are particularly preferred. As primary aliphatic amines which can be used in the process according to the invention, mention may be made of n-propylamine, isopropylamine, n-butylamine, isobutylamine, t-butylamine, pentylamine and isoamylamine. Among these amines, most particular preference is given to amines in which the alkyl chain is branched, and more especially to the tert-alkylamines corresponding to the general formula (I)

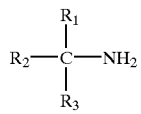

in which $R_1$, $R_2$ and $R_3$ represent C1–C8 alkyl groups. Amines corresponding to formula (I) are, in particular, t-butylamine and the tert-alkylamines Primene® 81-R and JM-T sold by the Rohm & Haas Company. t-Butylamine is most particularly preferred.

The catalyst-cocatalyst system preferred according to the present invention is the system composed of a copper (II) compound formed with an acidic organic compound and a primary amine in which the carbon atom next to the $NH_2$ group is a quaternary carbon atom, i.e. one without a hydrogen atom. The catalyst-cocatalyst system formed by copper (II) acetylacetonate and t-butylamine is particularly preferred.

The molar ratio between the cocatalyst and the olefin is generally greater than or equal to 0.01. Preferably, this molar ratio is greater than or equal to 0.05. Advantageously, this molar ratio is greater than or equal to 0.1. However, this molar ratio is usually less than or equal to 2. Preferably, this molar ratio is less than or equal to 1. Advantageously, this molar ratio is less than or equal to 0.5. The amount of cocatalyst used can vary, on a molar basis, from about 0.1 to about 25 times the amount of catalyst, preferably from about 0.5 to about 20 times.

It is understood that the above catalyst/olefin and cocatalyst/olefin ratios are expressed, in a batchwise process, relative to the total amount of olefin used, and, in a continuous process, relative to the stationary amount of olefin present in the reactor.

Generally, the reaction takes place at a temperature greater than or equal to room temperature. Preferably, the temperature is greater than or equal to 50° C. Advantageously, the temperature is greater than or equal to 70° C. However, the temperature is generally less than or equal to 200° C. Preferably, the temperature is less than or equal to 175° C. Advantageously, the temperature is less than or equal to 150° C. Most particular preference is shown for a temperature less than or equal to 120° C., or even 100° C.

The reaction time in a batchwise process or the residence time in a continuous process depend on various parameters, such as the reaction temperature, the concentration of reactants and of catalyst in the reaction mixture and their molar ratios. In general, depending on these parameters, the residence time or the reaction time can vary from 5 minutes to 10 hours. Advantageously, in a batchwise process, the reaction time is generally greater than or equal to 30 minutes, with a preference for reaction times of greater than or equal to 60 minutes.

However, the reaction time is usually less than or equal to 10 hours, with a preference for reaction times of less than or equal to 8 hours.

The pressure is generally chosen so as to maintain the reaction medium in the liquid phase. The pressure used varies depending on the temperature of the reaction medium. The pressure is usually greater than or equal to atmospheric pressure and less than or equal to 10 bar.

The examples below illustrate the invention in a non-limiting manner.

EXAMPLES 1–6

1,1,1,3,3-Pentachloropropane was prepared starting with vinyl chloride (VC) and carbon tetrachloride, by reaction between these reactants in the presence of a copper (II) compound and an amine or acetonitrile. To do this, the reactants, the catalyst and the amine or the acetonitrile were introduced into a 300 ml autoclave whose inner walls are lined with Teflon.

The apparatus was then closed hermetically, placed in a vertical oven and the temperature was raised gradually and maintained at 90° C. for the duration of the reaction. Stirring was provided by a magnetic bar placed in the bottom of the autoclave. At the end of the reaction, the autoclave was allowed to cool and a sample of liquid was taken by syringe and assayed by a chromatographic method in order to determine the degree of conversion of the olefin and the selectivity towards halohydrocarbon (1+1 product). The results obtained are collated in Table I.

EXAMPLES 7–10

The experimental procedure for the above examples was repeated with 2-chloro-1-propene (2-CPe) instead of VC, in the presence of copper (II) acetylacetonate as catalyst and tert-butylamine as cocatalyst, for a reaction time of 0.5 h at 90° C. The results obtained are also featured in Table II.

TABLE I

| Test No. | [CCl$_4$] (1) | amine (2) | [amine] (1) | solvent | [solvent] (1) | Cu salt (3) | [CuX] (1) | T, °C. | t, h | Conv. VC, % | Salt, % | Prod. mol/kg$_{sol}$/h |
|---|---|---|---|---|---|---|---|---|---|---|---|---|
| 1 | 1.8 | tBuAm | 0.2 | — | — | Cu(acac)$_2$ | 0.02 | 90 | 6 | 97 | 87 | 0.38 |
| 2 | 1.2 | tBuAm | 0.2 | — | — | Cu(acac)$_2$ | 0.02 | 90 | 6 | 97 | 77 | 0.45 |

TABLE I-continued

| Test No. | [CCl₄] (1) | amine (2) | [amine] (1) | solvent | [solvent] (1) | Cu salt (3) | [CuX] (1) | T, °C | t, h | Conv. VC, % | Salt, % | Prod. mol/kg$_{sol}$/h |
|---|---|---|---|---|---|---|---|---|---|---|---|---|
| 3(C) | 1.2 | — | — | AcN | 2.5 | Cu(acac)₂ | 0.022 | 130 | 13 | 99 | 44 | 0.10 |
| 4(C) | 1.2 | — | — | AcN | 2.5 | Cu(acac)₂ | 0.022 | 130 | 3 | 85 | 30 | 0.23 |
| 5 | 1.9 | PR81R | 0.16 | — | — | Cu(HFacac)₂ | 0.009 | 90 | 1.5 | 93 | 98 | 1.56 |
| 6 | 1.5 | PRJMT | 0.15 | — | — | Cu(HFacac)₂ | 0.008 | 90 | 1.5 | 90 | 98 | 1.65 |

(1) The concentrations are given as a molar ratio relative to the VC
(2) tBuAm = tert-butylamine;
PR81R = Primene ® 81R;
PRJMT = Primene ® JM-T
(3) Cu(acac)₂ = copper acetylacetonate;
Cu(HFacac)₂ = copper hexafluoroacetylacetonate

TABLE II

| Tests | CCl₄/2-CPe | Cu(acac)₂/2-CPe | t-BuAm/2-CPe | Conv. 2-CPe, % | Selectivity % | Prod., mol PCBa/kg$_{sol}$/hu h |
|---|---|---|---|---|---|---|
| 7(C) | 5.8 | 0.06 | 0.21 | 98 | 98 | 2.2 |
| 8 | 1.9 | 0.02 | 0.23 | 98 | 95 | 4.3 |
| 9 | 1.6 | 0.02 | 0.22 | 97 | 94 | 4.9 |
| 10 | 1.3 | 0.02 | 0.19 | 97 | 92 | 5.4 |

What is claimed is:

1. A process for the preparation of halohydrocarbons comprising at least 3 carbon atoms, by catalytic reaction between a haloalkane selected from the group consisting of dichloromethane, chloroform, carbon tetrachloride and 1,1,1-trichloroethane and a haloolefin, of the formula

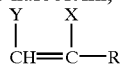

in which Y represents H or Cl, X represents Cl or F and R represents H, Cl, F or CH₃ characterized in that the reaction is carried out in the substantial absence of nitrile and with a molar ratio between the haloalkane and the haloolefin of less than 2 and the reaction is carried out in the presence of a catalytic system comprising a catalyst selected from the group consisting of an amine, amide and a trialkylphosphine oxide.

2. The process according to claim 1, in which the molar ratio between the haloalkane and the haloolefin is greater than or equal to 0.7.

3. The process according to claim 1, which further comprises at least one copper compound.

4. The process according to claim 3, in which the copper compound is a copper (II) compound.

5. The process according to claim 3, wherein the copper compound is copper (II) chloride, copper (II) hydroxychloride, copper (II) acetylacetonate or copper (II) hexafluoroacetylacetonate or mixtures thereof.

6. Process according to claim 1, wherein the catalyst is an amine.

7. Process according to claim 1, wherein the process is carried out continuously.

8. Process according to claim 2, wherein the process is carried out continuously.

9. The process according to claim 2, which further comprises at least one copper compound.

10. The process according to claim 9, wherein the copper compound is copper (II) chloride, copper (II) hydroxychloride, copper (II) acetylacetonate or copper (II) hexafluoroacetylacetonate or mixtures thereof.

11. The process according to claim 10, wherein said catalyst is in an amine.

12. The process according to claim 11, wherein the process is carried out continuously.

13. The process according to claim 1, wherein said catalyst is an amine and said process further comprises at least one copper compound.

14. The process according to claim 13, wherein said halohydrocarbon is 1,1,1,3,3-pentachlorobutane.

15. A process for the preparation of halohydrocarbons of the formula $$C_nH_{(2n+2)-p}Cl_p$$

where r is an integer form 3 to 4 and p is an integer rom 3 to 7, comprising a catalytic reaction between a haloalkane selected from the group consisting of dichloromethane, chloroform, carbon tetrachloride and 1,1,1-trichloroethane and a haloolefin, characterized in that the reaction is carried out in the substantial absence of nitrile and with a molar ratio between the haloalkane and the haloolefin of less than 2 and the reaction is carried out in the presence of a catalytic system comprising a catalyst selected from the group consisting of an amine, amide and a trialkylphosphine oxide.

16. The process according to claim 15, wherein the haloolefin corresponds to the formula

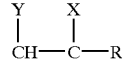

in which Y represents H or Cl, X represents Cl or F and R represents H, Cl, F or CH₃.

17. The process according to claim 16, in which Y represents H, X represents Cl and R represents H or CH₃.

18. The process as claimed in claim 1, wherein said halohydrocarbons are of the formula $$C_nH_{(2n+2)-p}Cl_p$$

where n is an integer from 3 to 4 and p is an integer from 3 to 7.

* * * * *

UNITED STATES PATENT AND TRADEMARK OFFICE
CERTIFICATE OF CORRECTION

PATENT NO. : 6,441,256 B1  
DATED : August 27, 2002  
INVENTOR(S) : Mathieu et al.

It is certified that error appears in the above-identified patent and that said Letters Patent is hereby corrected as shown below:

Column 6,
Line 37, delete "r" and insert -- n --.

Signed and Sealed this

Twenty-sixth Day of November, 2002

Attest:

Attesting Officer

JAMES E. ROGAN
Director of the United States Patent and Trademark Office